United States Patent [19]

Ross et al.

[11] Patent Number: 4,690,142

[45] Date of Patent: Sep. 1, 1987

[54] METHOD AND SYSTEM FOR UTILIZING ELECTRO-NEURO STIMULATION IN A BIO-FEEDBACK SYSTEM

[76] Inventors: Sidney A. Ross, 6901 Katherine Ave., Van Nuys, Calif. 91405; Lyn P. Taylor, 18300 Subido, Rowland Heights, Calif. 91748

[21] Appl. No.: 215,027

[22] Filed: Dec. 10, 1980

[51] Int. Cl.$^4$ ............................................. A61N 1/08
[52] U.S. Cl. ................................ 128/419 R; 128/733; 128/905
[58] Field of Search ............... 128/731, 732, 733, 905, 128/1 C, 419, 421, 422

[56] References Cited

U.S. PATENT DOCUMENTS

| | | | |
|---|---|---|---|
| 3,032,029 | 5/1962 | Cunningham | 128/732 |
| 3,495,596 | 2/1970 | Condict | 128/732 |
| 3,942,516 | 3/1976 | Glynn et al. | 128/732 |
| 3,967,616 | 7/1976 | Ross | 128/1 C |
| 3,991,304 | 11/1976 | Hillsman | 128/905 |

*Primary Examiner*—William E. Kamm
*Attorney, Agent, or Firm*—Blakely, Sokoloff, Taylor & Zafman

[57] ABSTRACT

An improved method and means for bio-feedback training of living organisms, utilizing one or more electro-neuro signals to produce tactile sensations on the skin of the organism. One or more electrical characteristics of such electro-neuro signals are responsive to a particular condition of the organism which is detectable in a physiological signal produced by the organism at a selected location on its body. The tactile sensation experienced by the organism is, thus, a function of the detected condition, and the organism can learn to alter such condition by concentrating on increasing or inhibiting the tactile sensation.

39 Claims, 4 Drawing Figures

METHOD AND SYSTEM FOR UTILIZING ELECTRO-NEURO STIMULATION IN A BIO-FEEDBACK SYSTEM

BACKGROUND OF THE INVENTION

1. Field of the Invention

This invention relates in general to the field which has become known as the bio-feedback field. In particular, a means for producing an electro-neuro signal, and a method for utilizing the same in a bio-feedback system as the stimulus to the living organism, is disclosed.

2. Prior Art

It has been discovered that a living organism, typically an animal high on the intelligence scale, can control its brainwave and nervewave patterns and bring about permanent or long lasting changes thereto by a process of learning; and, further, that the changes induced in the bioelectrical patterns can be such as to result in the substantial control of epileptic seizures, hyperkinesis and insomnia. This therapeutic approach has also been shown to be useful in correcting motor disorders such as the loss of motor control attributable to a spinal cord lesion. The prior art provides methods and systems enabling the application of this discovery in many fields including neurological therapy and brain research.

One invention in this field, disclosed in Ross' U.S. Pat. No. 3,837,331, teaches a means and method whereby a single bioelectrical signal is detected at a specific topological location in the nervous system of a living organism. Means are disclosed for detecting a particular electrical characteristic of interest in the single signal and, if it is present, feeding back to the organism a sensory indication of its presence. By this means and method, the organism can be trained to alter the waveform pattern of a bioelectrical signal detected in its nervous system.

A subsequent invention, disclosed Ross U.S. Pat. No. 3,967,616, teaches a method for training a living organism to alter multiple characteristics in the waveform pattern of a single bioelectrical signal, or multiple characteristics in the waveform patterns of a plurality of such signals. The second invention was based upon the discovery that a living organism can learn to alter multiple characteristics of one or more bioelectrical signals in its nervous system at the same time, thereby achieving new and beneficial results. In view of this discovery, the second invention teaches a means and a method by which such multiple-characteristic alteration training can be carried out.

Both of the foregoing inventions, and most other prior art bio-feedback systems and methods, typically utilize visual and/or aural bio-feedback means to effect the desired training. It has been found, however, that some patients do not respond well to either of these conventional bio-feedback stimuli. In particular, young patients, patients that have difficulty understanding instructions, and patients with receptive aphasia fall into this category. In addition, when a visual feedback is used, the patient must continuously observe a display. Such observation becomes tiring to the patient. When aural feedback is used, it has been found that patients may become habituated to it within minutes. Thus, the patient may not be able to produce the desired characteristics unless he is interacting with the bio-feedback apparatus. Tactile stimulation has also been tried as the feedback stimulus by means of mechanical (vibrational) stimulation of the epidermis. However, the means for such vibrational stimulation suffer from several disadvantages; namely:

(i) when the vibrations are increased to a high enough level to produce a tactile sensation, they often cause muscular contractions; the latter interfere with the training by introducing spurious bioelectrical signals.

(ii) a vibrational device must be attached securely to the patient's body, which introduces attachment difficulties;

(iii) attachment difficulties may be reduced by attaching the vibrational device to an extremity, but this necessarily limits the choice of locations for the tactile stimulation; and (iv) the difficulties of varying the AC power to the vibrational device as a function of the amplitude of the electrical signal representing the characteristic of interest has resulted in the use of heavy D.C. batteries, with the attendant disadvantage of their voltage decreasing with time and depletion.

To overcome these problems, the present invention teaches the use of an electro-neuro signal as the bio-feedback stimulus. Electro-neuro feedback is substantially less susceptible to the foregoing disadvantages of prior art means and methods. It should also be realized that electro-neuro feedback may be combined with visual and/or aural feedback when desired.

Patients tested with such electro-neuro stimulation have achieved, with remarkable rapidity, the benefits of bio-feedback training. Heretofore, in bio-feedback training, the utilization of an electro-neuro signal stimulus having the particular characteristics herein disclosed has not been used in lieu of, or in addition to, conventional visual or aural stimuli.

BRIEF SUMMARY OF THE INVENTION

Physiological functions of a living body produce a variety of physical manifestations such as, for example, pressure of the blood and other body fluids; variable electrical conductivity of the skin; temperature; and bio-electrical signals produced by neurological and muscular activity. Bio-electrical signals are generated in specific topological regions of the nervous system of a living organism, usually a human being or other intelligent animal. Typical means for detecting such physiological signals include electroencephalograph (EEG) instruments, polygraph instruments, electromyograph (EMG) instruments, electromyometer (EMM) instruments, temperature measurement instruments and galvanic skin response (GSR) instruments. Those physiologically based phenomena which are not electrical, e.g., blood pressure, require conventional transducers to convert them to electrical signals having characteristics, such as amplitude or frequency, which are proportionally or otherwise related to the original phenomenon. Such transducers are well known in the art.

Once a bio-electrical signal is detected, the prior art discloses many means for detecting the presence or absence of particular characteristics of the physiologically based signals, including conventional frequency filters, rectifiers, integrators and amplitude comparators. These prior art systems also disclose a variety of transducer means for producing a visual and/or aural stimulus to the organism undergoing biofeedback training. Thus, for example, when the presence of desirable characteristics, orthe absence of undesirable characteristics, is detected in the waveform pattern of the signal, the organism is stimulated with counters, lights coming on, a light becoming brighter, a bell ringing, and often, combinations of the above.

The present invention teaches the use of electro-neuro stimulation of the organism undergoing bio-feedback training in lieu of, or in addition to, conventional visual and/or aural stimulation as the feedback medium. The electro-neuro stimulation is an electrical signal which is applied directly to the organism's epidermis by means of surface electrodes. The electrical stimulation is sensed by means of the organism's tactile sensory apparatus. The subject, utilizing his cognitive powers, learns to alter particular characteristics of the detected physiological phenomenon or signal by concentrating upon increasing or inhibiting the intensity of the electro-neuro stimulation. By means of the design of the bio-feedback system being used, an increase in the intensity of the electro-neuro stimulus may be directly related to the presence of the desired characteristics in the physiological signal (e.g., a particular brain wave frequency) and/or the absence of the undesired characteristic thereof (e.g., a blood pressure above a pre-designated level). Alternatively, if the electro-neuro stimulation is introduced to a part of the body where it feels unpleasant (e.g., the stomach), then an increase in the intensity thereof would be related to the presence of an undesirable characteristic in the physiological signal.

Preferred means for producing a suitable electro-neuro signal for use as the sensory stimulus in bio-feedback training, and the characteristics of such signal, are described in detail below.

Thus, the present invention enables bio-feedback training to be successfully accomplished in instances where prior art systems and methods, based upon the feedback of visual and/or aural stimuli, have been less effective or not successful. Although a preferred embodiment of the invention is described hereinbelow, and shown in the accompanying drawings, it is expressly understood that the description and drawings thereof are for the purpose of illustration only and do not limit the scope of this invention.

BRIEF DESCRIPTION OF THE DRAWINGS

The present invention is now described in detail with reference to the accompanying drawings in which.

DETAILED DESCRIPTION OF THE INVENTION

Figures 1, 4:
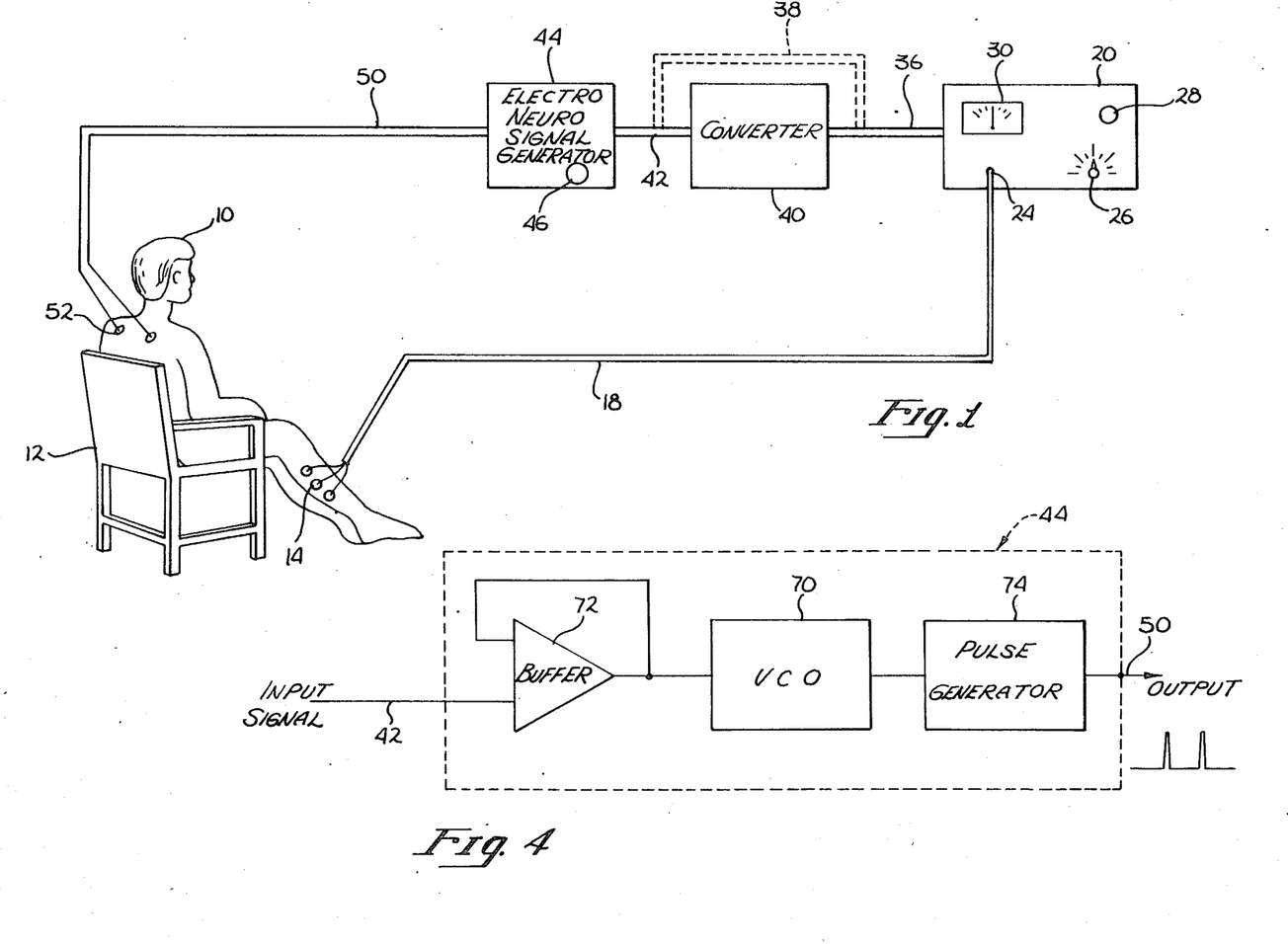
FIG. 1 is a block diagram of a bio-feedback system in which the present invention is utilized.
FIG. 4 is a block diagram of a circuit which produces a pulse train whose frequency is proportional to the characteristic of interest in the physiological signal.

With reference to FIG. 1, a bio-feedback system utilizing an EMG instrument for detecting a physiological signal and incorporating the present invention to produce electro-neuro stimulation for feedback to the patient, is now described in detail. The invented method will be described in conjunction with the description of the operation of the system shown. For purposes of the description, the living organism will be a human being 10, and more specifically a stroke rehabilitation patient who is undergoing biofeedback treatment for loss of neurological control of his right leg. Thus, the physiological signal of interest will be that generated by the patient's muscular activity in said leg. It should be understood, however, that the present invention is not limited in its application to electrical signals produced by muscular activity; nor to human beings; nor to stroke rehabilitation patients; nor to bio-feedback training in which a single topological region of the body is used for detecting physiological signals.

In FIG. 1 the human subject 10 is shown sitting in a comfortable chair 12. Electrodes 14 are attached to the patient's right leg. These electrodes are connected to an EMG instrument 20 by conductors 18 through a jack 24. Inasmuch as the muscular activity of the leg produces a bioelectrical signal, no transducer is required between the sensing electrodes 14 and the responsive instrument, EMG 20. A suitable EMG instrument is the Toomim Model 502A, which includes a gain control selector 26, a speaker 28 and a meter 30. The output of EMG instrument 20, which appears on output conductors 36, is proportional to the magnitude of the detected bioelectrical signal produced by the muscular activity of the subject's leg.

The inventors have discovered that highly effective means for stimulating a patient in the process of bio-feedback training is by means of an electro-neuro signal applied directly to a selected part of the subject's body. Such electro-neuro stimulation is used in lieu of, or in addition to, conventional visual and/or aural stimulation of the subject in the feedback process. The present invention teaches the use of a series or train of electrical pulses to provide said electro-neuro stimulation. A pulse train which has produced satisfactory results is one having the following characteristics: (i) a peak amplitude of at least 20 to 30 volts, this being the threshold voltage necessary to cause sufficient conduction of faradic current through the electrical resistance of the subject's epidermis to achieve a tactile sensation; (ii) a frequency in the range from 0.5 to 1000 Hz; and (iii) a pulse width of approximately 0.1 millisecond.

The present invention teaches the generation and feedback of an electro-neuro signal of the kind described above, wherein either the amplitude, the frequency or the pulse width, or some combination thereof, is related to one or more characteristics of interest in the detected physiological signal. Thus, for example, in the illustration shown in FIG. 1, it is the object of the bio-feedback training to train the subject 10 to make controlled movements of his right leg. When so activated, that portion of the subject's musculature system involved generates bioelectrical signals readily detected by the EMG instrument 20. The greater the amplitude of the EMG detected signal, the greater the electro-neuro stimulation wnich is fed back to the patient.

Means are disclosed hereinbelow for producing a variable level of electro-neuro stimulation which is a direct function of the amplitude of the EMG, detected bio-electrical signal. As indicated above, this invention is not limited to providing electro-neuro stimulation which is responsive to the amplitude of the physiological signal, but can just as readily be made responsive to any other detectable characteristic, or combination of characteristics, of interest in the physiological signal. Moreover, by the means disclosed in the Ross U.S. Pat.

No. 3,967,616, the variable electro-neuro stimulation may be made responsive to the presence and/or absence of multiple characteristics of one or more physiological signals.

With reference to FIG. 1, an electro-neuro signal generator 44 is shown incorporated into the bio-feedback loop. It is electrically coupled in series to the output of EMG instrument 20. Converter means 40 is also shown in the bio-feedback loop depicted in FIG. 1. It is electrically connected in series between EMG instrument 20 and electro-neuro signal generator 44. The input signal to converter means 40 is carried by conductors 36, while its output is connected to the input of generator 44 by conductors 42.

The purpose of converter means 40 is to provide a proper electrical signal to electro-neuro signal generator 44 in those applications in which the signal output by the signal responsive instrument 20 is not compatible. For example, in the embodiments of electro-neuro signal generator 44 disclosed hereinbelow, the required input signal is a variable analog (D.C.) voltage whose amplitude is a function of the presence and/or absence of the characteristic(s) of interest in the detected physiological signal within, a pre-determined voltage range. Thus, if the output signal from the responsive instrument 20 (which is an EMG in FIG. 1 only for purposes of illustration) is sinusoidal, or outside the range of the input voltage required by generator 44, convertor means 40 becomes necessary to achieve compatibility. Moreover, converter means 40 may also include additional characteristic detection means which may not be incorporated in the responsive instrument 20. Thus, for example, if it is important to detect whether a particular characteristic of interest persists for at least a pre-determined duration, and if timing means for determining said duration are not incorporated in instrument 20, then such timing means would be incorporated in converter means 40. In view of the foregoing, converter means 40 may comprise within it the electronic signal processing components in the configurations disclosed by Ross in his U.S. Pat. Nos. 3,837,331 and 3,967,616. Such components may include an operational amplifier, half-wave rectifier, filters, gain control means, timing circuits and logic means, all adapted and configured to provide a suitable output for input to the electro-neuro signal generator 44; i.e., a variable D.C. voltage whose amplitude is a function of the presence and/or absence of the characteristic(s) of interest in the detected physiological signal. Other feedback configurations of converter means 40, each of which depends upon the training application, are well known to persons skilled in the art, and a description of any particular configuration is not necessary for the proper understanding or practice of the present invention.

In some applications, the responsive instrument 20 may be suitable for directly connecting its output to the input of the electro-neuro signal generator 44. In such instances, no converter 40 is required. The latter configuration is symbolized by conductors 38, shown in phantom lines.

Figure 2:
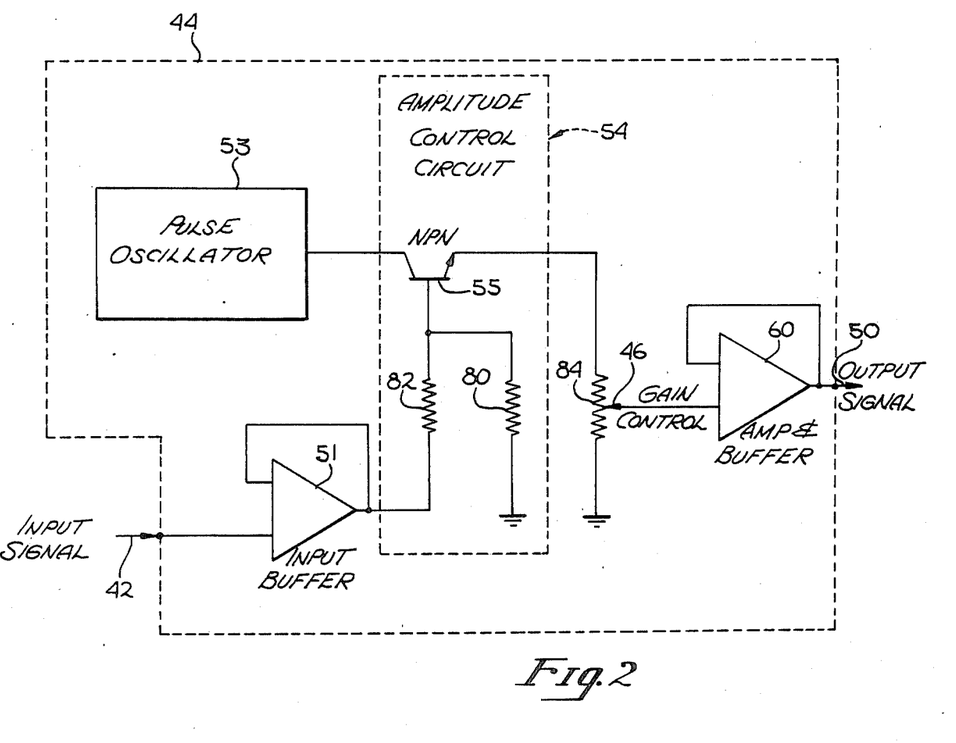
FIG. 2 is a block diagram of a circuit which produces an electro-neuro feedback signal comprising a pulse train whose amplitude is proportional to the characteristic of interest in the physiological signal.

With reference to FIG. 2, an embodiment is shown of an electro-neuro signal generator 44, designed to generate a pulse train whose amplitude is directly proportional to the amplitude of the analog signal input thereto (and, therefore, proportional to the intensity of the characteristic of interest in the detected physiological signal). A conventional pulse generator 53 which generates a pulse train having the requisite pulse width, frequency and amplitude, is electrically connected to an amplitude control circuit 54. Amplitude control circuit 54 comprises an NPN transistor 55 whose (i) collector is connected to the output of pulse generator 53; (ii) base is connected to ground potential through a suitable resistor 80, and coupled to the input signal on conductors 42 through resistor 82 and a suitable input buffer 51; and (iii) whose emitter is connected to gain control means, preferably a potentiometer 84. The output of gain control means 84 is electrically coupled to an output amplifier and buffer 60, which feeds back the electro-neuro stimulation to the subject 10, through output conductors 50 and electrodes 52. Output amplifier and buffer 60 is typically a conventional operational amplifier with gain. Gain control means 84 is set by control knob 46 to limit the maximum amplitude produced by this embodiment of the electro-neuro signal generator.

In operation, when the amplitude of the input signal is below the threshold of transistor 55, the transistor does not conduct, and none of the pulses generated by generator 53, and appearing at its collector, are passed to the output amplifier and buffer 60. The appearance of an input signal whose amplitude is above the threshold of transistor 55 causes conduction of the transistor, the conductivity of the transistor being a function of the input voltage at its base. In effect, transistor 55 operates as a variable resistor, dividing the amplitude of the pulses output by generator 53 between the voltage drop across the transistor and that across gain control means 84. The higher the amplitude of the input voltage, the greater the conductivity of transistor 55, and therefore, the greater amplitude of the input voltage, up to a maximum value determined by the setting of gain control means 84. The selection of particular values and components for the above-described circuit will be readily apparent to circuit designers of ordinary skill in the art.

A commercially available circuit, which can be readily modified to produce a suitable electro-neuro signal generation of the kind shown in FIG. 2, is the transcutaneous nerve stimulator ("TNS") Model 1500, marketed by Ntron Electronics of San Raphael, Calif., under the trademark NTRON. The NTRON TNS produces an electro-neuro signal; namely, a pulse train of constant frequency, amplitude and width, adapted to stimulate the sensory nerve endings in the skin. One of its primary applications is to block pain from the particular part of the body to which its output is applied. The modification of the NTRON TNS is the inclusion of the input buffer 51, whereby the input signal received from the responsive instrument 20 (directly or through converter means 40) controls or determines the amplitude of the electro-neuro stimulation fed back to the subject 10 (up to a maximum determined by the setting of the gain control means 84). In addition, when an application requires the variable electro-neuro stimulation to be in bursts of pre-selected or random periods, rather than continuous, conventional timing means for controlling the output periods of the pulse train (not shown) are readily available in the electronic trade.

Figure 3:
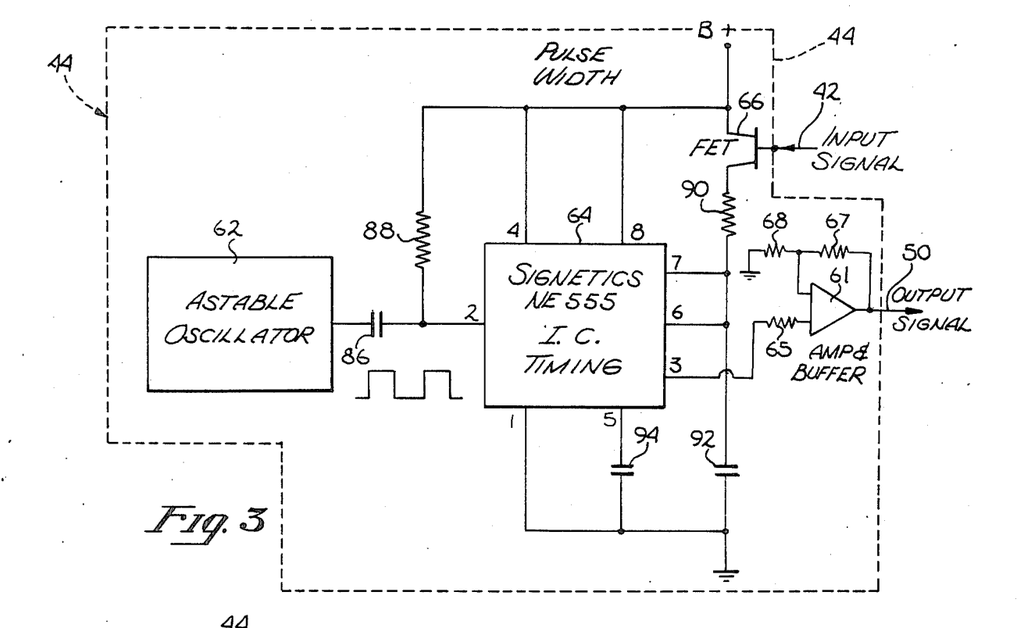
FIG. 3 is a block diagram of a circuit which produces an electro-neuro feedback signal comprising a pulse train whose pulse width is proportional to the characteristic of interest in the physiological signal.

In FIG. 3, an electro-neuro signal generator 44 is shown, which is adapted to output a pulse train whose pulse width is a function of the magnitude of the input signal output by converter means 40, or directly by responsive instrument 20, as the case may be. In this embodiment, a conventional astable oscillator 62, which generates a square wave of the desired frequency, is electrically coupled to the input of a conventional timing circuit 64, such as the I.C. NE 555 sold by Signetics, through capacitor 86. (The input terminal of a Signetics NE 555 circuit is number 2). The drain of a field effect transistor ("FET") 66 is coupled to the same D.C. power supply (B+) which powers the timing circuit 64. In addition, said B+ is coupled to terminal 2 through resistor 88 and directly to terminals 4 and 8 of the Signetics timing circuit 64. The input signal 42 is connected to the gate of FET 66. FET 66 is electrically connected in series with an RC circuit comprised of resistor 90 and capacitor 92 between B+ and ground. Terminals 6 and 7 of the Signetics timing circuit 64 are connected to the common point between resistor 90 and capacitor 92, while terminals 1 and 5 are coupled to ground potential directly and through capacitor 94 respectively. The output pulses from Signetics timing circuit 64 appear on terminal 3, and are coupled to amplifier and buffer 61 through resistor 65. Amplifier and buffer 61 is typically a conventional operational amplifier with gain. Feedback resistor 67, which couples the output of amplifier and buffer 61 to one of its inputs, and resistor 68, which couples said input to ground, set the voltage gain of amplifier and buffer 61. The output pulses produced by amplifier and buffer 61 are fed back to the patient 10 through output conductors 50 and electrodes 52.

In the embodiment of electro-neuro signal generator 44 depicted in FIG. 3, the variable resistance presented by FET 66 results in a variable RC time constant, which determines the duration of the pulses generated within the timing circuit 64 initiated by the negative edges of the square wave appearing on terminal 2, and therefore, the pulse width of the pulse train. The resistance of the FET 66 is, in turn, determined by the amplitude of the input voltage appearing on conductors 42 and at the gate thereof (which input signal is an analog of the characteristic(s) of interest in the physiological signal), the greater the conductivity of the FET 66, the lesser the time constant, and thus, the narrower the pulse width. As the pulse width of the electro-neuro signal varies, the tactile sensation experienced by the subject 10 varies. As a consequence, the subject 10 can learn to beneficially affect the characteristic(s) of interest by concentrating on enhancing or inhibiting the sensations produced by the pulse train with the variable pulse widths. If, for example, an increase in the amplitude of the input signal represents a greater intensity of a desirable condition, the subject 10 would be trained to concentrate on achieving the tactile sensation produced by an electro-neuro signal with pulses having a narrower width, i.e., on increasing the input signal level. The selection of particular values and components for the above-described circuit will be readily apparent to circuit designers of ordinary skill in the art.

Another variable parameter of the pulse train which constitutes the electro-neuro stimulation is its frequency. By means of the configuration shown in FIG. 4, a pulse train whose frequency is a function of the amplitude of the input signal on conductors 42 may be produced. In this configuration, the input signal on connectors 42 is electrically coupled to a conventional, voltage controlled oscillator ("VCO") 70 through a suitable buffer 72, such as the operational amplifier No. LM 358 sold by National Semiconductor. The VCO 70 produces a periodic signal whose frequency is a function of the amplitude of the input signal. The output of the VCO is connected to the input of a suitable pulse generator 74, such as a one shot multivibrator, which is adapted to produce a pulse train having a fixed amplitude and pulse width, and whose frequency corresponds to that of the output signal of VCO 70. The pulse train so generated is fed back to the subject 10 by stimulation conductors 50. Circuits of the foregoing kind are well known in the electronics art.

An output coupling transformer (not shown) may be added at the output of the electro-neuro signal generator 44 to allow stepping up the stimulation voltage, when the generator 44 is operated from low voltage battery power.

The present invention also contemplates the use of electro-neuro stimulation by pulse trains whose frequency, amplitude and/or pulse width are variables determined by the magnitude of the analog input signal or signals, thereby producing different tactile sensations. By altering such sensations, the subject 10 in bio-feedback training can learn to enhance desirable characteristics and/or reduce undesirable characteristics of interest in the physiological signal detected by electrodes 14. Such a multi-variable pulse train can be produced by combining the circuits shown in FIGS. 2, 3 and 4, or by designs readily apparent to circuit designers of ordinary skill.

The output of the electro-neuro signal generator 44 is conducted by conductors 50 to electrodes 52 placed on the skin of the subject 10. In the illustration shown in FIG. 1, the electro-neuro signal is applied to the back of the subject 10. It should be understood that the invention is not limited to providing the electro-neuro stimulation to the subject's back, nor to its application to only one topological region of the body. In this connection, in most instances it is important to place the electrodes 52 as far away as possible from the electrodes 14 which detect the original physiological signal. For example, if the bio-feedback training relates to achieving muscular control in one arm, the opposite arm would be a suitable location for the electro-neuro stimulation to be fed back to the subject. However, this invention also contemplates, in suitable applications, placing the feedback electrodes 52 substantially adjacent to the detection electrodes 14. In addition, in placing electrodes 52, one should avoid so-called "motor points" which, when stimulated by the electro-neuro signal, may cause muscular contractions. The latter could adversely affect the bio-feedback training by introducing unwanted sensations and spurious bioelectrical signals. Obviously, electrodes 52 should not be placed on any part of the body which has or may have reduced sensory capacity, such as, for example, the paralyzed side of a stroke rehabilitation patient.

The teachings of the present invention may be applied in many ways depending upon the problem being confronted, the age and condition of the subject, among other factors. The therapist must decide whether the electro-neuro stimulation of the subject is to be a comfortable or pleasant sensation, or an uncomfortable, or even slightly painful, sensation. This decision is a factor to be considered in determining the site of placement of the feedback electrodes 52. For example, placement on the abdomen generally results in an uncomfortable sensation. This would be the preferred location when the selected training modality requires the patient to concentrate on inhibiting the tactile sensation. Placement of electrodes 52 on the back often produces a pleasant sensation, and thus, would be the preferred location when the selected training modality requires the subject to concentrate on increasing the pleasant tactile sensation, in contrast to inhibiting an unpleasant one.

The inventors have found that electro-neuro signals of higher frequencies are generally more comfortable than signals at lower frequencies; that signals with wider pulse widths are more uncomfortable than those with narrower pulse widths; and that the signals with greater amplitudes produce a sharper and more uncomfortable sensation than those with lower amplitudes. However, as indicated above, the topological location on the subject's body where the stimulation electrodes 52 are placed is an important factor in determining whether the tactile sensation experienced is comfortable or uncomfortable.

In the application illustrated in FIG. 1, the patient feels the sensation produced by an electro-neuro signal whose amplitude is the variable. Thus, he becomes aware that he is producing a desirable EMG detected bio-electrical signal in his right leg. He is encouraged to produce a stronger sensation, which is indicative of a higher amplitude EMG signal at the leg (amplitude being the characteristic of interest). In this patient, the electro-neuro stimulation on the upper back is generally pleasant, notwithstanding that it is a sharper feeling, and the training modality selected was to encourage the patient to concentrate on increasing the sensation. Note further that the gain control means 26 of the responsive instrument 20 is adjusted to accommodate the expected amplitude range of the EMG signal. Moreover, gain control means 84 of the electro-neuro signal generator 44 is adjusted by knob 46 to limit the maximum amplitude of the electro-neuro signal to a level which remains comfortable for the subject 10.

The present invention is equally applicable in applications where EEG signals are detected; also, in addition to bio-feedback training relating to EEG and EMG physiological signals, other physiological signals which can be used (after being suitably transduced) include body temperature, galvanic skin response, gastro-intestinal activity, blood pressure, heart rate, respiration, taste, touch, vocalization, pain, neurogenic activity or any other bodily function, or any combination thereof.

The present invention contemplates still further variations of the electro-neuro stimulation fed back to a subject in the process of bio-feedback training. For example, circuits can be readily designed by circuit designers to generate discrete, rather than proportional, levels of stimulation as a function of the presence, duration, intensity, discrete level and/or absence of a characteristic of interest in a physiological signal of interest. In addition, the electro-neuro stimulation may be produced for pre-determined periods of time, i.e., in bursts, where such periods may occur periodically or in a random pattern. Further, the electro-neuro stimulation may be made to vary in discrete steps rather than continually in response to variations in the characteristic(s) of interest, and such discretely stepping electro-neuro stimulation may be applied to the subject 10 in bursts which are periodic or which occur in a random pattern, as aforesaid. Any of the foregoing combinations of continual or discrete variation of the electro-neuro stimulation, and its application to the subject in a continuous, periodic or random manner can be readily implemented by conventional timing, logic, control and gating circuits.

The present invention further contemplates the use of multiple electro-neuro signal generators 44 in multiple channel bio-feedback applications. The simultaneous training of antagonistic muscle pairs is an example of a multiple channel application. Multiple channel stimulation can be used to produce different sensations in response to the detection of different characteristics of interest in one or more physiological signals with respect to which the training is undertaken; alternatively, multiple channel stimulation can also be used to produce different sensations in response to detection of the same characteristic in two or more physiological signals, or combinations thereof.

Multiple channel, electro-neuro stimulation may be applied to two or more separate locations on the subject's body, or at one location, or a combination thereof, as appropriate to provide to the subject tactile information about the characteristic(s) of interest. For example, a first sensation caused by electro-neuro stimulation can be used to indicate a desired condition, and a second one to indicate concurrently an undersirable condition. Multiple channel, electro-neuro stimulation may also be used to produce a unique tactile sensation by combining the outputs of two signal generators 44 and feeding the combined signal back to the subject 10. In yet another embodiment of multiple channel, electro-neuro stimulation, a first sensation may be produced at a location on the subject's body, in response to the detection of a particular characteristic of interest in one or more physiological signals, which sensation may then be altered in response to a separately detected characteristic(s) of interest in the same or other physiological signals. The altered sensation may be achieved by reducing, increasing modulating or turning off or any combination thereof the electro-neuro signal which produces the first sensation.

Another application of electro neuro-stimulation is to feed back to the subject 10 a free-running electro-neuro signal at a nominal level, and then to reduce, increase, modulate or turn off the same, or any combination thereof, in response to a detected characteristic of interest in one or more physiological signals.

The great variety of possible applications of the inventive concepts disclosed herein require corresponding configurations which can be implemented readily by those having ordinary skill in the art. At the heart of all such configurations is at least one electro-neuro signal generator 44. Such generator 44 may be integrated with conventional timing circuits, gating and logic circuits, amplitude control circuits and/or modulators so as to implement the desired application.

It is known that the tactile sense of human beings is highly sensitive, and that humans probably pay more attention to what they feel than to what they hear or see. For this reason, electro-stimulation of the tactile sense has been viewed as a potentially fruitful medium for enhanced bio-feedback training. However, heretofore, those skilled in the bio-feedback art have experienced, or believed, that tactile stimulation would adversely affect the training process by interfering with the primary physiological signal of interest. The present invention, however, teaches means and methods for advantageously utilizing the highly sensitive tactile sense in bio-feedback training, without the adverse effects feared by others in the field.

Other variations and applications of this invention will be apparent to persons skilled in this field without departing from the spirit and scope thereof. The present invention, therefore, is not intended to be limited to the particular method and means disclosed herein.

We claim:

1. In a method for controlling the nervous system of a living organism, including the steps of (i) detecting at least one physiological signal from at least a first topological location on said organism; (ii) detecting at least one characteristic of interest in said physiological signal; and (iii) producing at least one output signal responsive to the detected characteristic of interest, the improvement comprising the steps of:

(a) generating at least one electro-neuro signal responsive to said at least one output signal;

(b) feeding back said electro-neuro signal to said organism by coupling the same to at least a second topological location on said organism, thereby producing a tactile sensation thereat; and (c) causing said organism to concentrate mentally so as to vary said tactile sensation at said second topological location and training said organism to alter said characteristic of interest of said physiological signal by said concentration, wherein at least one electrical characteristic of said electro-neuro signal is continually responsive to said at least one output signal, and said tactile sensation experienced by said organism continually varies as said electrical characteristic of said electro-neuro signal varies.

2. The improved method of claim 1 wherein said tactile sensation experienced by said organism varies as a function of the, duration of said detected characteristic of interest in said physiological signal.

3. The improved method of claim 1 wherein said electro-neuro signal produced is a pulse train, and said electrical characteristics thereof comprise frequency, amplitude and pulse width.

4. The improved method of claim 1, wherein said electrical characteristic of said electro-neuro signal is programmed to change in pre-determined discrete steps at predetermined times in response to said at least one output signal.

5. The improved method of claim 4 wherein said predetermined times occur in a random pattern.

6. The improved method of claim 1, wherein said electrical characteristic of said electro-neuro signal is programmed to change in discrete steps at pre-determined times in response to said at least one output signal, said discrete steps being to levels which form a random pattern.

7. The improved method of claim 6 wherein said predetermined times occur in a random pattern.

8. The improved method of claim 1 wherein said electro-neuro signal is fed back to said organism in discontinuous burst during pre-determined periods.

9. The improved method of claim 1 wherein said electro-neuro signal is fed back to said organism in discontinuous bursts during periods which occur in a random pattern.

10. The improved method of claim 1 wherein said at least one output signal comprises first and second output signals which are produced responsive to one characteristic of interest in at least two physiological signals, and wherein first and second electro-neuro signals are generated responsive to said first and second output signals, thereby producing first and second tactile sensations at said second topological location and at a third topological location respectively on said organism, said first sensation indicating a desired condition and said second sensation indicating a desirable condition.

11. The method defined by claim 10, wherein said second sensation indicates an undesirable condition.

12. The improved method of claim 1 wherein said at least one output signal comprises first and second output signals which are produced responsive to one characteristic of interest in at least two physiological signals, sand wherein first and second electro-neuro signals are generated responsive to said first and second output signals, including the additional step of combining said first and second electro-neuro signals and thereby producing a combined tactile sensation at a single topological location on said organism.

13. The improved method of claim 1 wherein said at least one output signal comprises first and second output signals which are produced responsive to one characteristic of interest in at least two physilogical signals including the additional steps of generating said electro-neuro signal in response to said first output signal, and alternating said electro-neuro signal in response to said second output signal.

14. The improved method of claim 13 wherein said alteration of said electro-neuro signal in response to at least one of said first and second output signals is a reduction of said electro-neuro signal.

15. The improved method of claim 13 wherein said alteration of said electro-neuro signal in response to said second output signal is an increase of said electro-neuro signal.

16. The improved method of claim 13 wherein said alteration of said electro-neuro signal in response to said second output signal is a modulation of said electro-neuro signal.

17. The improved method of claim 13 wherein said alteration of said electro-neuro signal in response to said second output is a turn off of said electro-neuro signal.

18. The improved method of claim 13 wherein said alteration of said electro-neuro signal in response to said second output signal is a reduction and modulation of said electro-neuro signal.

19. The improved method of claim 13 or 16 wherein said alteration of said electro-neuro signal in response to said second output signal is an increase and modulation of said electro-neuro signal.

20. The method by claims 10, 12, or 13 wherein said first and second output signals are produced responsive to at least two characteristics of interest in one physiological signal.

21. The improved method of claim 1 including the additional steps of generating a free-running electro-neuro signal, thereby producing a continuous tactile sensation in said organism, and altering said free-running electro-neuro signal in response to said at least one output signal.

22. The improved method of claim 21 wherein said alteration of said electro-neuro signal in response to said at least one output signal is a reduction of said electro-neuro signal.

23. The improved method of claim 21 wherein said alteration of said elctro-neuro signal in response to said at least one output signal is an increase of said electro-neuro signal.

24. The improved method of claim 21 wherein said alteration of said electro-neuro signal in response to said at least one output signal is a modulation of said electro-neuro signal.

25. The improved method of claim 21 wherein said alteration of said electro-neuro signal in response to said at least one output signal is a turn-off of said electro-neuro signal.

26. The improved method of claim 21 wherein said alteration of said electro-neuro signal in response to said at least one output signal is a reduction and modulation of said electro-neuro signal.

27. The improved method of claim 21 wherein said alteration of said electro-neuro signal in response to said at least one output signal is an increase and modulation of said electro-neuro signal.

28. The improved method of claim 1 wherein said first topological location and said second topological location on said organism are substantially adjacent.

29. The improved method of claim 1 wherein said tactile sensation experienced by said organism varies as a function of the intensity of said detected characteristic of interest in said physiological signal.

30. The improved method of claim 1 wherein said tactile sensation experienced by said organism varies as a function of the duration and intensity of said detected characteristic of interest in said physiological signal.

31. The method defined by claim 1, wherein said mental concentration inhibits said tactile sensation at said second topological location.

32. In a system for controlling the nervous system of a living organism comprising (i) means for detecting at least one physiological signal from at least a first topological location on said organism; (ii) means coupled to said detecting means for determining the presence of at least one characteristic of interest in said physiological signal; and (iii) means for producing at least one output signal responsive to the presence of said said characteristics of interest, the improvement comprising:

(a) means for generating at least one electro-neuro signal responsive to said output signal, coupled to said means for producing said output signal, wherein said electro-neuro signal generating means is arranged and configured so that at least one electrical characteristic of said electro-neuro signal is responsive to said output signal; and (b) means for coupling said electro-neuro signal to at least a second topological location on said organism, thereby porducing a tactile sensation thereat, whereby said organism is trained to alter said characteristic of interest of said physiological signal by concentrating mentally so as to vary said tactile sensation at said second topological location.

33. The improvement of claim 32 wherein said electro-neuro signal generating means is arranged and configured to generate a pulse train whose electrical characteristics comprise frequency, amplitude and pulse width.

34. The improvement of claim 32 where said detection means and said means for coupling said electro-neuro signal are disposed at substantially adjacent topological locations on said organism.

35. The improved system of claim 32 wherein said producing means produces at least one output signal responsive to the intensity of said characteristic of interest.

36. The improved system of claim 32 wherein said producing means produces at least one output signal responsive to the duration of said characteristic of interest.

37. The improved system of claim 32 wherein said producing means produces at least one output signal responsive to the intensity and duration of said characteristic of interest.

38. The improved system of claim 32 wherein said determining means determines the absence of at least one characteristic of interest in said physiological signal and said producing means produces an output signal response to said absence.

39. The system defined by claim 32, wherein said mental concentration inhibits said tactile sensation at said second topological location.

* * * * *

UNITED STATES PATENT AND TRADEMARK OFFICE
CERTIFICATE OF CORRECTION

PATENT NO. : 4,690,142
DATED : 09/01/87
INVENTOR(S) : Ross et al.

It is certified that error appears in the above-identified patent and that said Letters Patent is hereby corrected as shown below:

| COLUMN | LINE | DESCRIPTION |
|--------|------|-------------|
| 02 | 67 | delete "orthe" insert --or-- and --the-- |
| 12 | 12 | delete "physilogica" insert --physiological-- |

Signed and Sealed this

Tenth Day of January, 1989

Attest:

DONALD J. QUIGG

Attesting Officer     Commissioner of Patents and Trademarks